United States Patent [19]
Stein

[11] Patent Number: 4,811,373
[45] Date of Patent: Mar. 7, 1989

[54] BONE DENSITOMETER

[75] Inventor: Jay A. Stein, Framingham, Mass.

[73] Assignee: Hologic, Inc., Waltham, Mass.

[21] Appl. No.: 78,419

[22] Filed: Jul. 27, 1987

[51] Int. Cl.⁴ ............................................. G01B 15/02
[52] U.S. Cl. ...................................... 378/54; 378/56; 378/207; 378/146
[58] Field of Search .................................. 378/51–56, 378/110–112, 207, 62, 146, 204, 4, 16

[56] References Cited

U.S. PATENT DOCUMENTS

| | | | |
|---|---|---|---|
| Re. 28,544 | 9/1975 | Stein | 378/58 |
| 3,944,830 | 3/1967 | Dissing | |
| 3,996,471 | 12/1976 | Fletcher et al. | |
| 4,639,943 | 1/1987 | Heinze et al. | 378/112 |
| 4,641,331 | 2/1987 | Makimo et al. | 378/112 |

OTHER PUBLICATIONS

Wahner, et al., "Noninvasive Bone Mineral Measurements", Seminars in Nuclear Medicine, vol. XIII, No. 3, 1983.

Gustafsson, et al., "X-Ray Spectrophotometry for Bone-Mineral Determinations", Medical and Biological Engineering, Jan., 1974.

Sartoris, et al., "Bone Mineral Density in the Femoral Neck", American Journal of Roentgenology, 144, Mar. 1985.

"The Norland Dichromatic Bone Densitometer" [Distributed at trade show in Nov., 1985].

Cann, "A Clinician's Guide to the Use of Bone Mass Measurements" [Preprint: not known to have been published or presented publicly].

Dunn, et al., "Measurement of Bone Mineral Content in Human Vertebrae and Hip by Dual Photon Absorptiometry", Radiology, vol. 136, No. 2, pp. 485–487, Aug., 1980.

Primary Examiner—Carolyn E. Fields
Assistant Examiner—Joseph A. Hynds

[57] ABSTRACT

In an x-ray bone densitometer, special calibration techniques are employed to accommodate variations. In one aspect, a bone-like calibration material is interposed and the system determines the calibration data from rays passing only through flesh. In another aspect, a rotating device carries the calibration material through the beam. The specific densitometer shown uses an x-ray tube operated at two different voltages to generate a pencil beam, the energy levels of the x-ray photons being a function of the voltage applied. An integrating detector is timed to integrate the detected signal of the patient-attenuated beam over each pulse, the signals are converted to digital values and a digital computer converts the set of values produced by the raster scan into a representation of the bone density of the patient. Multiple reference detectors with differing absorbers are used by the system to continuously correct for variation in voltage and current of the x-ray tube. Calibration is accomplished by the digital computer on the basis of passing the pencil beam through known bone-representing substance as the densitometer scans portions of the patient having bone and adjacent portions having only flesh. A set of detected signals affected by the calibration substance in regions having only flesh is compared by the computer with a set of detected signals unaffected by the calibration material.

36 Claims, 8 Drawing Sheets

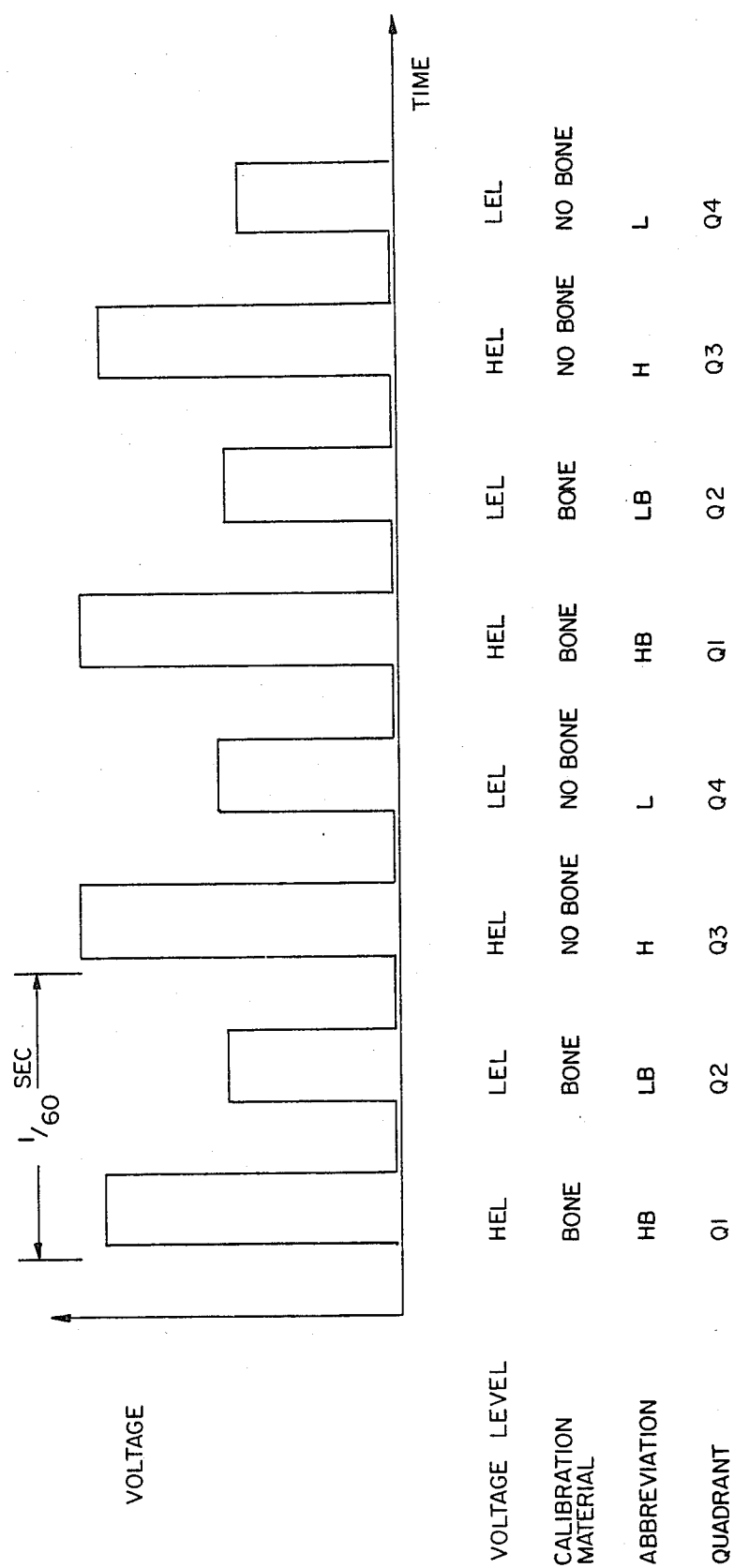

STEP 15

BONE DENSITOMETER

The invention is an x-ray densitometer suitable to measure bone density, or density of bone like materials, in the human body, particularly in the spine and hip. Such measurements are useful, e.g. for determining whether patients are affected by osteoporosis. The invention uses a measurement technique which is an improvement over a related technique called dual-photon absorptiometry. Dual photon absorptiometry is based on the use of radioisotopic sources to provide photons of two different energies whereas the present invention uses an x-ray tube switched between two different voltages in order to generate a collimated beam of two different energies.

An x-ray source is capable of producing an intensity of radiation about 1000 times greater than conventional radioisotopic sources used for bone density measurements. If an x-ray source were successfully incorporated in a bone densitometer, an improvement in measurement time, resolution, accuracy, precision, and minimization of radiation dose might be effected. Prior efforts to use x-ray sources for bone densitometers have not been altogether successful. A major purpose of the present invention is to provide a successful bone densitometer and to achieve improved performance in all of the important categories by taking advantage of the high radiation intensity produced by an x-ray source.

The invention achieves this objective by use of an x-ray tube which is moved in a 2-dimensional raster scanning pattern with a fixed relationship between the tube and a collimator and detector which move with it, with alternating high and low voltage levels being applied to the x-ray tube.

In order to take optimal advantage of the high photon intensity provided by x-ray sources, the invention overcomes certain problems associated with using x-ray tubes for bone densitometry. Although x-ray sources are more intense than radioisotopic sources, they are also less stable because they vary (drift) with changes in the voltage and current supplied to them. In addition, x-ray tubes produce photons that have a broad range of energies whereas radioisotopic sources typically produce photons with only a few energies.

These and other problems are met by a system which employs two reference detectors instead of one, means for providing frequent bone calibration, e.g. on every scan line, preferably on every point, and use of an integrating detector in the raster scan.

An important feature of the invention is a calibration technique which determines the location of bone and then calibrates the system on the basis of x-ray data produced from non bone areas that lie close to the location of bone. Such calibration not only accomodates drift of the x-ray source but also other variations encountered, such as variation in body thickness from patient to patient.

To summarize, according to one aspect of the invention, a bone densitometer is provided for measuring density of bone-like material in a patient who is held in fixed position, comprising an x-ray tube means having a power supply, detector means arranged on the opposite side of the patient to detect x-rays attenuated by the patient, means to effectively expose portions of the patient having bone and adjacent portions having only flesh (non-bone body substance), means for causing the beam to pass through a bone like calibration material in the course of the exposure, and signal processing means responsive to the output of the detector means to provide a representation of bone density of the patient (e.g., an x-ray film like picture of the patient, showing bone density distribution or calculated values representing bone density of the patient), the signal processing means adapted to respond to data based upon x-rays attenuated by the calibration material in regions having only flesh to calibrate the output of the detector means, thereby enabling the accommodation of drift in the x-ray tube, differences in patient thickness and other system variations.

According to another aspect of the invention, a bone densitometer, e.g., having the features described above, further comprises a pencil beam collimator arranged to form and direct a pencil beam of x-rays through the patient, and the detector means, on the opposite side of the patient, is aligned with the collimator, the x-ray tubes, pencil beam collimator and detector means adapted to be driven in unison in an X Y raster scan pattern relative to the patient, and rotating means cause the beam to pass through bone-like calibration means. According to this aspect of the invention, the signal processing means is not limited to responding to data based upon x-rays attenuated by the calibration material in regions having only flesh to calibrate the output of the detector means.

According to another aspect of the invention, a bone densitometer incorporates features of both of the above described aspects of this invention.

In preferred embodiments of these aspects of the invention, the power supply of the bone densitometer is adapted to apply alternate high and low voltage levels to the x-ray tube; control means for the frequency of the voltage is related to the speed at which the x-ray tube, collimator and detector means are driven in scan motion and the beam width produced by the collimator to apply alternating high and low voltage levels to the x-ray tube at a frequency sufficiently high that at least one pair of high and low level exposures occurs during the short time period during which the pencil beam traverses a distance equal to about one beam width, preferably the bone densitometer being adapted to produce pairs of high and low voltage pulses at a rate of the order of sixty per second, the x-ray tube, collimator and detector means being driven along the scan at a rate of the order of one inch per second and the collimator produces a pencil beam of between about one and three millimeters in diameter; the x-ray beam passes through the bone-like calibration material at least once per scan line of a scan pattern for a period equal to at least the time during which one pixel of resolution is traversed, preferably the x-ray beam passes through the bone-like calibration material for the duration of every other high and low voltage pulse pair; the detector means comprises an integrating detector controlled to integrate the detected signal repeatedly over short time periods relative to the time required to advance the x-ray scan pattern by one pixel of resolution, preferably an analog to digital converter being provided to convert each integrated value, to a digital signal and a digital computer means is provided for producing the representation of bone density of the patient by processing the stream of the digital signals; and a reference system is provided having at least two reference detectors each provided with a different absorber, the reference system adapted to correct for both x-ray tube current and voltage changes, preferably the system adapted to correct the detected signal substantially on the basis of a function of the signals produced by the reference detectors and, where there are two of the reference detectors, the function being substantially a straight line defined by the detected signals of the reference detectors.

The present invention makes it possible to perform bone density measurements more rapidly and with better resolution and accuracy than prior devices. Because it does not use radioisotopic sources, the user does not need to handle and replace radioactive materials which are dangerous and are strictly controlled by federal licensing regulations.

In the drawings:

FIG. 2a illustrates the scan pattern employed by the preferred embodiment while

FIG. 5 is an illustration of the voltage levels produced during the high energy level (HEL) and low energy level (LEL) phases of energization of the x-ray tube as modified by the synchronized calibration wheel having "bone" and "no bone" quadrants;

DESCRIPTION OF THE PREFERRED EMBODIMENT

Figure 1:
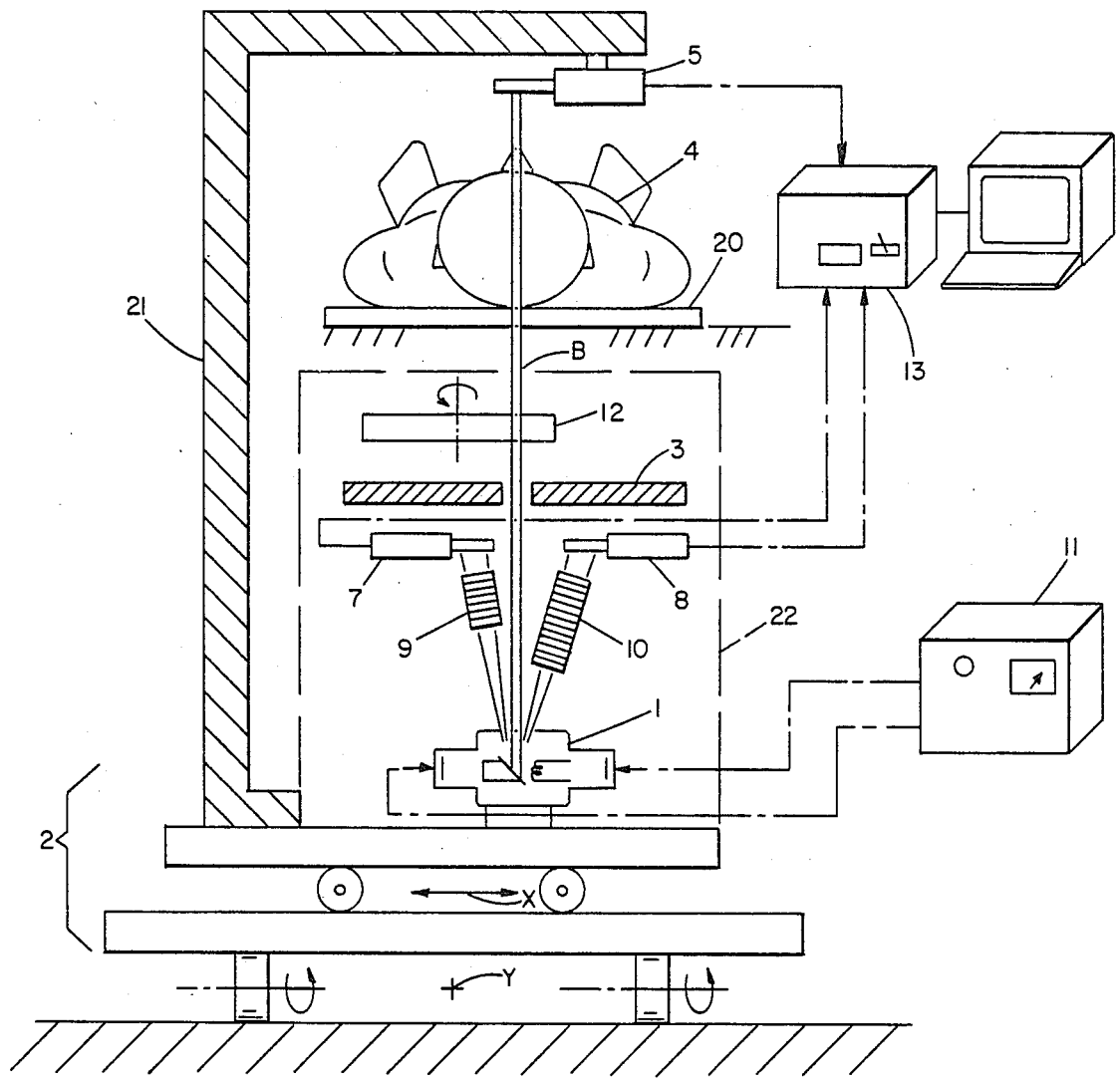
FIG. 1 is a diagrammatic illustration of the preferred embodiment.

FIG. 1 shows the basic components of the x-ray densitometer. X-ray tube 1 carried on x-y table arrangement 2 is energized by power supply 11 which is designed to alternate its voltage output rapidly between two levels called the "High Energy Level" (HEL) and the "Low Energy Level" (LEL). The HEL is typically 150 kilovolts and the LEL is typically 75 kilovolts. The x-rays emitted by the x-ray tube are collimated to form a pencil beam B by collimator 3. The pencil beam passes through a calibration disc 12 which rotates at a rate which is synchronized with the rate at which the power supply 11 switches between the HEL and LEL. The role played by the calibration disc will be described below.

The x-ray pencil beam passes through, e.g., a female adult patient 4 under examination for possible presence of osteoporosis and impinges on a main radiation detector 5. Two reference detectors 7 and 8 which are similar in design to the main detector 5 are also shown in FIG. 1. The reference detectors 7 and 8 monitor the flux emitted by x-ray tube 1 and provide information used to correct the signal measured by main detector 5 for variations in the x-ray tube current and voltage.

The reference detectors 7 and 8 measure radiation from the x-ray tube 1 after it has traversed one of two x-ray absorbers 9 and 10. The two absorbers 9 and 10 are of substantially different thicknesses which are typically chosen to be representative of the x-ray attenuation of a thin patient and a heavy patient respectively. By using two reference detectors with different absorbers it is possible to monitor changes simultaneously in both the x-ray tube current and voltage. The reference detector measurements are used to correct the measurements made with the main detector 5 in order to compensate for these changes in tube current and voltage. The manner in which these corrections are made is described below.

Figure 2:
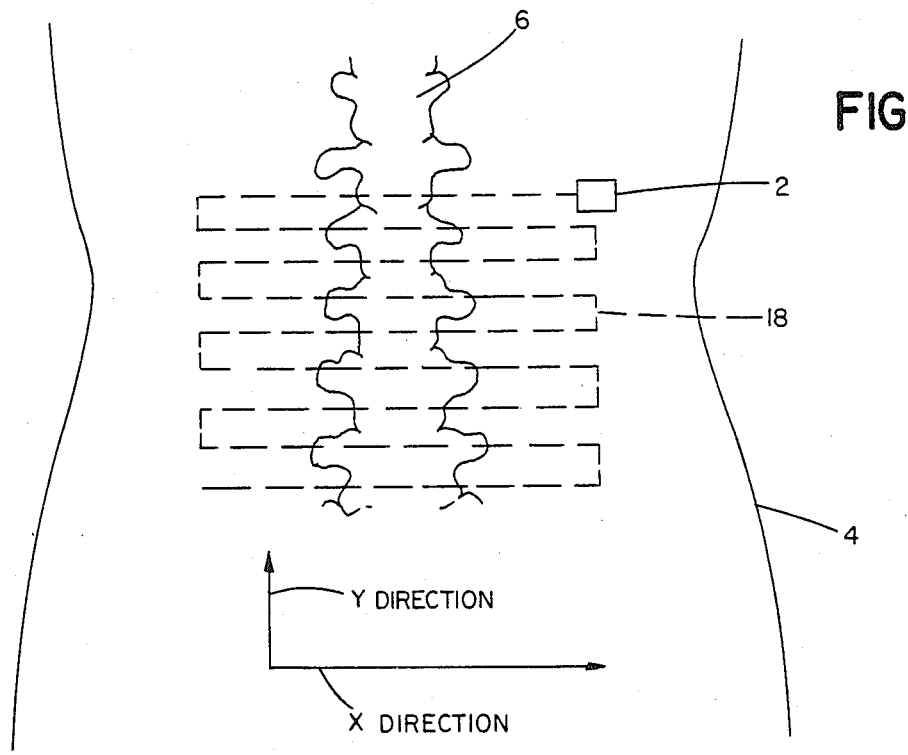
FIG. 2 represents a patient's spine with superposed scan pattern.
Figure 2A:
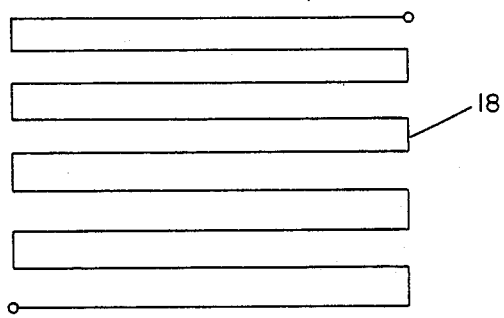
Figure 2B:
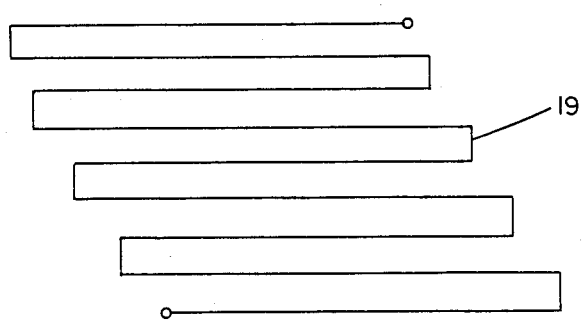
FIG. 2b illustrates an alternative scan pattern.

X ray tube 1, collimator 3, reference detectors 7 and 8 and absorbers 9 and 10, calibration disc 11, and main detector 5 are all mechanically continuously scanned in the X direction across the body during which time signals from the main detector 5 and reference detectors 7 and 8 are digitized and stored in computer system 13. After each scan from right to left or left to right in FIG. 1 the assembly briefly stops moving in the X direction, and is indexed a small amount in the Y direction, out of the plane of FIG. 1. As a result of these motions, the pencil x-ray beam B undergoes a rectangular scanning pattern 18 such as shown in FIGS. 2 and 2a. A modified rectangular scanning pattern shown as parallelogram pattern 19 in FIG. 2b might also be used to measure a bone such as the neck or the femur, which is set at an angle in the human body.

FIG. 1 illustrates the fixed relationship between the x-ray source 1 and main detector 5 during the scanning period throughout which patient 4 lies stationary on patient table 20. X ray tube 1, collimator 3, reference detectors 7, 8 and absorbers 9 and 10, and calibration disc 12 are mounted together in a single assembly called the source assembly 22. This assembly is mounted in turn below the patient on a conventional X-Y table 2. Separate stepping motors and lead screws are used to move the X Y table in the X direction and Y-direction respectively. The stepping motors and lead screws are of a type well known in the art and are not shown.

The main detector 5 is mounted above the patient and in the preferred embodiment shown is rigidly attached by means of C arm 21 to the source assembly 22 so that x-ray pencil beam B and main detector 5 have a fixed relationship throughout the scan. The main detector 5, in alternative embodiments, could be driven with its own drive system in either the X-direction, Y-direction or both so long as it maintains the same fixed relationship to pencil beam B.

In FIG. 2, a representation of the patient's spine 6 and adjacent portions of the body is shown. In general, pencil beam B scans from side to side across the patient's spine, and through flesh on either side of the spine, but does not pass beyond the outer dimensions of the adult patient 4. The total distance scanned from side to side (i.e. in the X-direction) is typically 5 inches and the total distance scanned from head to toe (i.e. in the Y-direction) is typically 5 inches.

During the scanning period, the signals from detector 5 and from reference detectors 7 and 8 are digitized and stored in computer system 13. It is possible to calculate the bone density at each point in the scan pattern from these data using a method described in more detail below. Both the raw data and the calculated bone density can be displayed as an image using any one of a number of devices well known in the art. Such an image will resemble a conventional x-ray image or radiograph. In a preferred embodiment, the computer system 13 contains one such device known as a display processor which displays the image acquired in this manner on a television screen. Devices such as a display processor or other computer peripherals such as laser printers are well known devices for displaying images from digital data.

Figure 3:
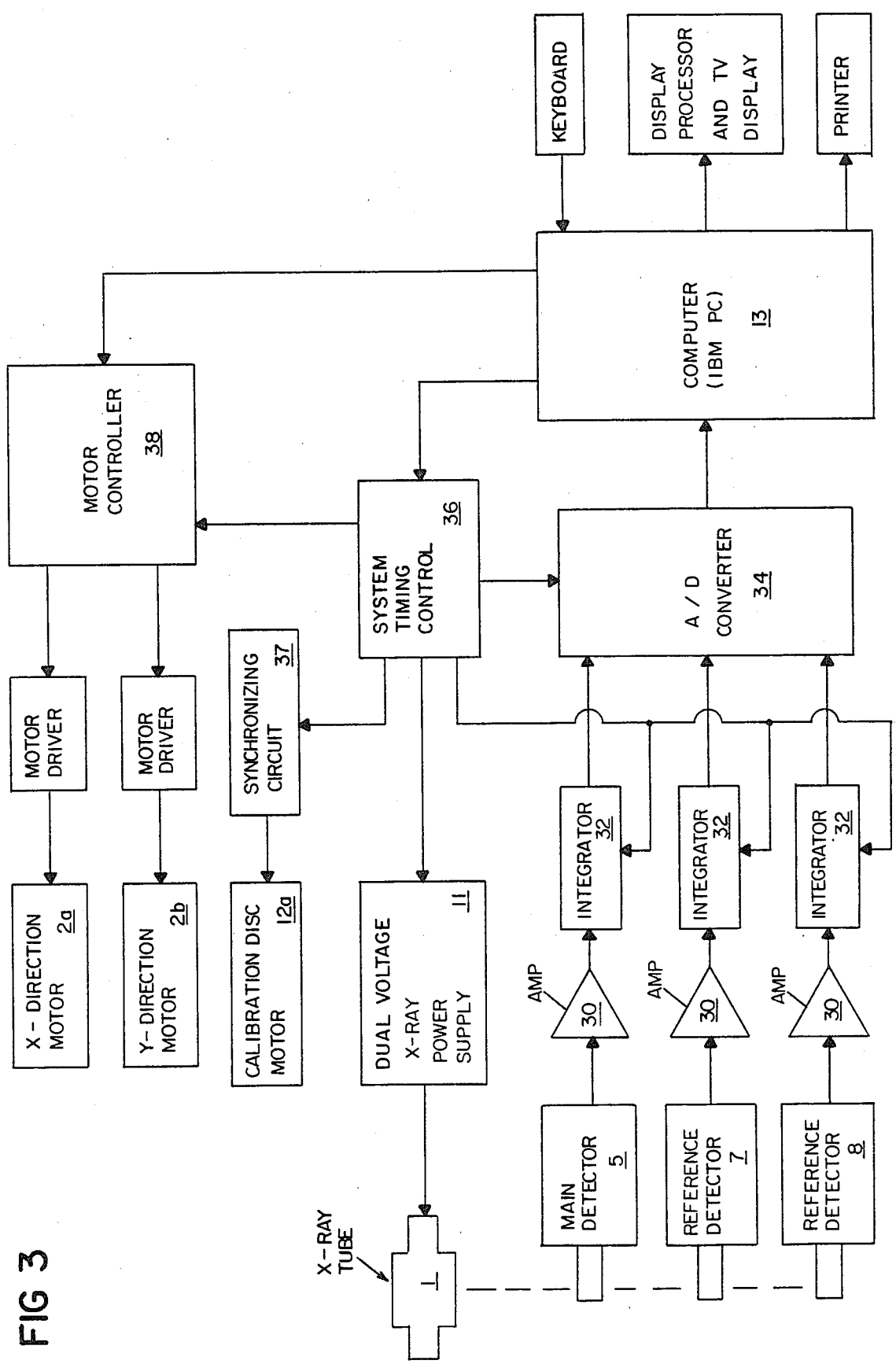
FIG. 3 is a block diagram of the electronic control and measuring system of the preferred embodiment.

FIG. 3 is an electronic block diagram of the bone densitometer showing the relationship between the different components of the system. X-ray photons striking the crystals in the scintillation detectors 5, 7, 8 generate optical radiation which is converted by the detector photomultiplier tubes into electrical currents. These in turn are amplified and converted to voltage levels by individual amplifiers 30. The amplifier outputs are integrated by respective integrators 32 for time periods that are controlled by the system timing control 36 about which more will be said. The output of the three integrators are digitized by an analog-to-digitial converter 34 and stored for processing in a small computer 13 such as an IBM PC or AT computer system.

The system timing control 36 synchronizes the x-ray power supply pulsing and the signal integrators. For example, just before a HEL voltage is applied to the x-ray tube, all three integrators are reset to zero. As the HEL is applied to the x-ray tube, radiation is emitted and all three integrators begin to integrate signals. A short time later (typically 1/120 second), the system timing control terminates the HEL voltage level, terminating the emission of x-radiation. This is immediately followed by a signal generated by the timing control which terminates the integration of detector signals and causes the A/D converter to digitize the integrator output and transfer the digital value to the computer system. A similar sequence of timing signals is then generated for the next LEL pulse after which the cycle is repeated.

The system timing control 36, in addition to the functions described above, also provides a means to synchronize, via synchronizing circuit 37, the calibration disc motor 12a to assure that the rotation frequency of the calibration disc 12 and the x-ray pulsing frequency are locked together so that the timing relationships illustrated in FIG. 5 are maintained. The timing control in a preferred embodiment also provides a pulse sequence to the stepping motor controller 38 which drives X and Y-direction motors 2a and 2b and assures that every scan line in the x-ray image has exactly the same number and phasing of x-ray pulses.

The computer 13 provides scan distance instructions to the stepping motor controller 38 and scan initiation instructions to the system timing control 36 and allows the operator to initiate, manipulate, and terminate the raster scan motion and x-ray generation by means of a standard keyboard. It records the digitized detector information, calculates bone density for each point in the raster scan pattern, and displays the resulting image using a standard computer display processor and television monitor. Hardcopy versions of the calculated and displayed bone density can be obtained with a standard printer interfaced to the computer.

BEAM SIZE AND SWITCHING FREQUENCY

During the scanning of the x-ray pencil beam B, the voltage on the x-ray tube 1 is switched between the HEL and LEL. A typical speed used to continuously scan across the patient from side to side is 1 inch per second and a typical switching frequency for the x-ray tube power supply is 60 cycles per second. In this case there will be 60 HEL pulses alternating with 60 LEL pulses generated during each one second of scanning. The signals from detectors 5, 7 and 8 are recorded separately for the HEL pulses and for the LEL pulses. For a scan speed of 1 inch per second, one HEL/LEL pair of measurements is made for every 1/60 of an inch (0.016 inch) traversed by the pencil beam.

The cross sectional area of the pencil beam B is determined by the opening in collimator 3 and is typically 1–3 mm (0.040–0.120 inch) so that there are typically 2½ to 8 HEL/LEL pulse pairs per beam width. One of the important features of the present invention is that there is at least about one pulse pair per beam width. As a result, the small region of the body sampled by the pencil beam during the HEL measurement will be essentially the same as the small region of the body sampled by the LEL measurement made 1/120 second later.

USE OF INTEGRATING DETECTORS

The detectors used in the preferred x-ray densitometer are of a type generally known as scintillation detectors, although use of a number of other types of detectors is also possible. A scintillation detector consists of a crystal material coupled to a photomultiplier tube. The crystal serves to convert x-ray radiation to optical radiation and the photomultiplier tube converts the optical radiation to an electronic signal. Solid state photodiodes coupled to x-ray fluorescent screens, ionization chambers, and other devices might also serve as radiation detectors for the present invention.

In dual-photon bone densitometers using radioisotopes, scintillation detectors are also used as radiation detectors. However, in these devices, the detectors must detect individual x-ray photons and sort these photons into two separate channels corresponding to high-energy photons and low-energy photons. This requirement for performing a spectrum analysis on individually detected photons is dictated by the fact that the isotopic source emits both high-energy and low energy photons simultaneously.

In the present invention, the scintillation detector used need not perform a spectrum analysis task by sorting photons into high and low-energy channels because the high-energy and low-energy photons are not emitted simultaneously. Rather the HEL and LEL voltages are generated alternating in time. The high-energy and low-energy photons are integrated separately over the duration of the HEL and LEL pulses respectively and are therefore recorded at different times.

The ability to use energy integrating detectors rather than photon counting detectors is an important feature of the x-ray densitometer because it makes it possible to complete a patient scan in a short time. In order to measure bone density to a given accuracy, it is necessary to detect a resulting minimum number of photons because the statistical accuracy of a measurement is related, as is well known, to the square root of the number of detected photons. For example, at least 50–100 million photons are typically detected in a bone density measurement of the spine.

The x-ray densitometer of the present invention completes a measurement scan in as little as 2 to 5 minutes. In order to record as many as 100 million photons in 2 minutes, the detector must record on the order of 1 million photons per second. By using energy integrating detectors rather than pulse counting detectors, the x-ray densitometer can record photon fluxes of 1 million per second or higher. (An energy integrating detector can easily record photon fluxes as high as 100 million photons per second.) The use of alternating high and low voltage pulsing of the x-ray tube, coupled with integrating detectors to measure the high-energy and low-energy signals produced, is an important feature of the present invention because it makes short scan times possible, which implies a shorter visit by patients and better use of capital equipment.

THE REFERENCE DETECTORS AND ABSORBERS

By use of two reference detectors, with different absorbers, small changes in both the x-ray tube current and applied voltage are effectively monitored along with the signals from the main detector. Just as the main detector integrates photons and supplies separate values for the HEL pulse and the LEL pulse, the reference detectors also supply separate reference values for each HEL pulse and LEL pulse. Each HEL or LEL measurement recorded by the main detector is corrected according to the following method.

Let P1 and P2 be the percentage changes in output signal (from a HEL or LEL pulse) measured by the first and second reference detectors respectively due to a small variation in x-ray tube current and voltage. Let T1 and T2 be the thicknesses of body tissue that attenuate the HEL or LEL pulses the same amount as do the first and second absorbers shown in FIG. 1 respectively. Each main detector signal corresponds to a body thickness T0, and is corrected by a percentage P0 which is given by the formula (P0−P1)=(P2−P1)/(T2−T1)*(T0−T1). (This can be recognized as the formula for a straight line fit between the measured values of P1 and P2.) This correction compensates the main detector measurement for changes in both x-ray tube current and voltage. This feature enables the main detector signal to be corrected for fluctuations in x-ray tube current and voltage that would otherwise degrade the accuracy of the bone density calculation, unless the x-ray power supply is quite stable over the duration of one patient scan. In the case that the power supply is sufficiently stable, the use of the reference detectors may be omitted. Longer term variations in x-ray tube current and voltage are compensated by the use of the calibration disc now to be described.

THE CALIBRATION DISC

Figure 4:
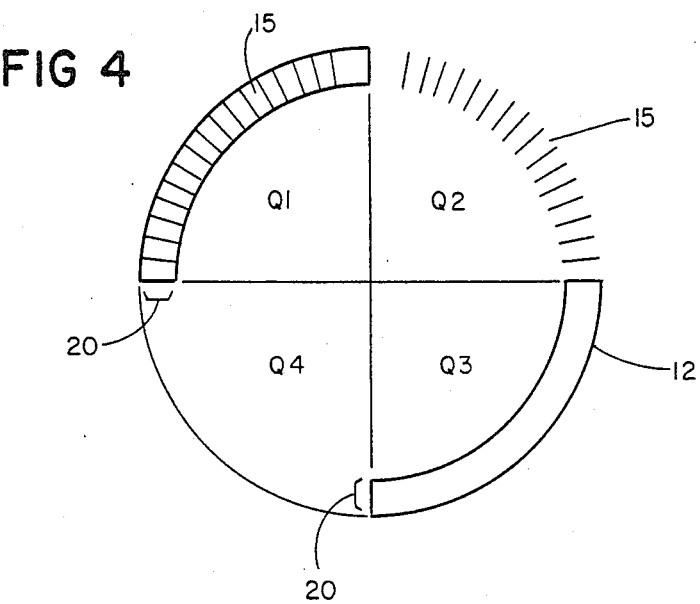
FIG. 4 is a plan view of the calibration disc employed in the preferred embodiment.

FIG. 4 is a plan view of the calibration disc 12 which is mounted such that the region of the disc near the circumference interrupts pencil beam B as the disc rotates. The calibration disc is synchronized to the switching frequency of the high voltage power supply. In a preferred embodiment, the power supply produces HEL and LEL pulses which are derived from the main power line frequency of 60 Hertz. The HEL and LEL pulses generated by the power supply in this embodiment are shown in FIG. 5. One pair of HEL and LEL pulses are generated every 1/60 of a second.

In the preferred embodiment, the calibration disc is driven with a synchronous motor which rotates at a rate of exactly 30 revolutions per second and which is adjusted in phase such that four pre-defined quadrants of the disc (labeled Q1, Q2, Q3, and Q4 in FIG. 4) correspond to the HEL and LEL levels being generated by the power supply. More specifically, when Quadrant 1 is obstructing the pencil beam the voltage level is HEL, when Quadrant 2 is obstructing the pencil beam the voltage level is LEL, when Quadrant 3 is obstructing the beam the voltage level is again HEL, and finally when Quadrant 4 is obstructing the beam the voltage level is again LEL. The desired synchronization between the quadrants of the calibration disc and the HEL/LEL voltage pulses is illustrated in FIG. 5.

In this preferred embodiment, the circumference of Quadrants 1 and 2 consists of a material which has the same x-ray attenuation characteristics as bone. Both quadrants contain exactly the same amount of the bone-like calibration material 15 which typically amounts to about 1 gram per square centimeter of material. As a result, every other HEL/LEL pulse pair recorded by the main detector is attenuated by a constant thickness of calibration bone, as the calibration bone rotates in and out of the x-ray beam. Using the calibration disc in this manner, four distinct types of measurements are periodically recorded from the main detector. These types and their abbreviations are (1) HEL and no calibration bone (H), (2) LEL and no calibration bone (L); (3) HEL with calibration bone (HB), and (4) LEL with calibration bone (LB). The four groups of measurements H, L, HB, and LB conditions are illustrated in FIG. 5.

One additional function of the calibration disc is worth noting. It is possible to make use of the same disc for the additional purpose of providing different x-ray filtration for the HEL and LEL x-ray beams. For example, in a preferred embodiment, the LEL beam is left unfiltered whereas the HEL beam is filtered with 1 mm of copper. The purpose of the copper filtration is to attenuate the HEL beam, which is typically of considerably higher intensity than the LEL beam because it suffers less attenuation in tissue. By attenuating the HEL beam, it is possible to avoid unnecessary x-ray exposure to the patient and thereby lower the dose without substantially affecting the accuracy of the final bone measurement.

In FIG. 4, in a preferred embodiment, Quadrants 1 and 3 contain the copper filtration in the form of a constant thickness sheet of copper 20 for the HEL beam and Quadrants 2 and 4 contain no filtration (or possibly another filtration material) for the LEL beam. The use of a rotating wheel to provide different x-ray filtrations is another advantage of the present invention, although the main purpose of the calibration disc is to provide continuous calibration of the densitometer as explained below.

CALCULATION OF BONE DENSITY

The method used to calculate bone density with high accuracy is based on dual photon absorptiometry calculations as described in prior publications. (See for example: "Noninvasive Bone Mineral Measurements," by Heinz W. Wahner, William L. Dunn, and B. Lawrence Riggs, *Seminars in Nuclear Medicine*, Vol. XIII, No. 3, 1983.) The x-ray densitometer described here uses a modification of the established method which makes use of the calibration disc bone-like material to obtain an absolute reference for making accurate and repeatable measurements of the real bone. The calibration disc measurements automatically and continuously calibrate the values calculated for bone density and thereby compensate for any short or long term drift in the x-ray detection electronics or other system variations, as well as differences in patient thickness.

Figure 6:
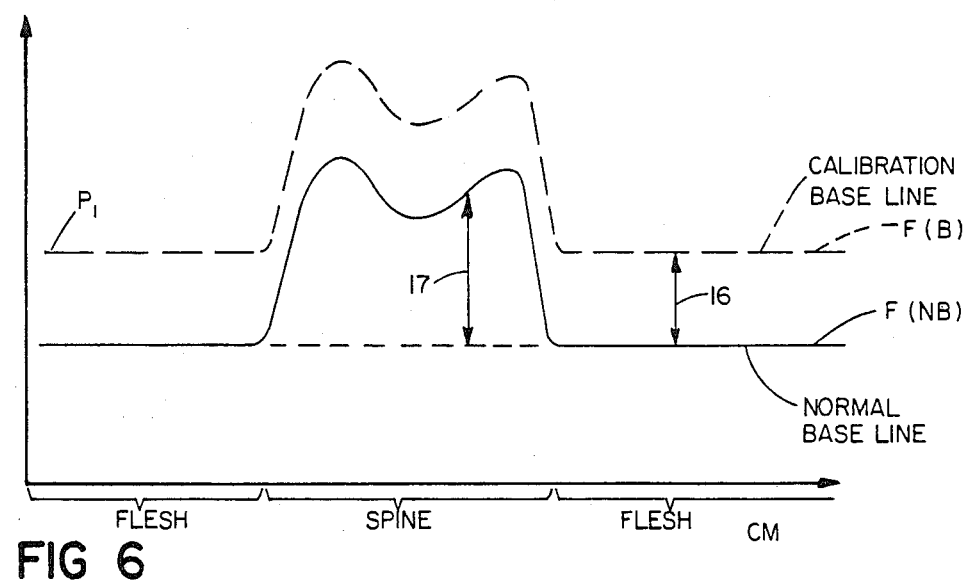
FIG. 6 shows a plot of a function derived from the "bone" and "no bone" pulse pairs for a single traverse of the spine.

FIG. 6 shows schematically a plot of the function F=ln(L)−k*ln(H) for both the "bone" and "no bone" pulse pairs for a single traverse across the spine. It is important for this calibration to traverse across at least some portions of the patient having only flesh adjacent to the spine. (Using the notation defined above to be more precise, the calibration bone version of F, F(B) is equal to ln(LB)−k*ln(HB) and the no calibration bone version of F, F(NB), is equal to ln(L)−k*ln(H).) In these formulae, the symbol, ln, indicates the natural logarithm function and the letter, k, is equal to the ratio of the attenuation coefficient of tissue for the LEL pulse to the attenuation coefficient of tissue for the HEL pulse. The values for H, L, HB, and LB used to calculate F in these formulae are the x-ray beam attenuation values measured by the main detector after corrections derived from the reference detector measurements have been applied. The reference corrections applied in this manner are given by the values for P0 as described above.

The Wahner et al. publication cited demonstrates that the value of the functions F(B) and F(NB) will be a constant if there is no bone or bone-like material (or other high atomic number material) in the beam path through the patient. This is strictly true if k is constant across the scan line, independent of patient thickness, and can be made to hold in practice by measuring any dependence of k on patient thickness and using the corrected value of k to calculate the function F. In FIG. 6, the resulting constant values obtained when the beam is on either side of the spine (i.e. passing through portions of the body having flesh, without bone) are labeled Calibration Baseline and Normal Baseline corresponding to the plots of the functions F(B) and F(NB) respectively. The increase in the value of the function, F, over and above each baseline level when the x-ray beam scans across the spine has been shown to be directly proportional to the amount of bone or bone-like material in the path of the beam.

In FIG. 6, the separation value 16 between the Normal Baseline and the Calibration Baseline can be calculated by finding the numerical average of the difference between F(B) and F(NB) for measurements made through portions of the body having only flesh on either side of the bone. This separation value is an important parameter in the operation of the densitometer because it calibrates the bone measurements in the spine directly against the known density of the bone-like calibration material which is used in the calibration disc measurements. Thus, the separation value corrects for both x-ray source drift, and for variations between different patients e.g. patient thickness, and other system variations. In FIG. 6, for example, suppose that a particular set of H/L measurements results in an F value (17 in FIG. 6) equal to 2.46 at the spine, and that the average separation value 16 at adjacent portions of the body has a value of 1.23. Then the bone density in the spine at the point where F equals 2.46 will be exactly (in this example) 2.00 times the of the bone-like calibration material used in the calibration disc.

Using the separation value 16 as a calibration constant, the spine bone density can be calculated for all measurement pairs H/L recorded during the entire two dimensional raster scanning of the patient without the need for precise mechanical positioning of the x-ray beam or the calibration bone. The resulting two dimensional array of bone density values can be displayed as an image using readily available computer peripherals.

Using the calibration disc to perform calibration measurements is the presently preferred method of calibrating the x-ray densitometer. Because calibration measurements are made numerous times for every scan line in the bone density image, one obtains assurance of proper calibration regardless of the location of the bone in the scan pattern. Other means of performing calibration measurements are possible and are comprehended by certain broader aspects of this invention. For example, if the pencil beam were brought to a rest at the end of each scan line or at the start or completion of the entire san a piece of bone-like material could be inserted in the beam and calibration data could be taken. Alternatively, the bone-like calibration material could be inserted into the beam on every alternate scan line. In another embodiment, a small amount of calibration material is placed under a part of the patient having only flesh without bone.

After the baselines have been determined for each scan line and the bone density image has been created, it is also useful to detect automatically the outer boundary of the spine for each scan line. From these data it is possible to calculate a number of useful parameters. For example, the integral of the bone density values (expressed in units of grams per square centimeter) between two pre determined scan lines (usually chosen to correspond for spine measurements to a fixed number of vertebral bodies) is called the total bone mineral content (expressed in grams) and is one often quoted parameter. The integral of bone density values over the entire region of interest divided by the area of the bone as determined by the outer boundaries of the spine is the area averaged bone mineral density (expressed in grams per square centimeter) and is another frequently cited parameter.

The means for determining baseline values for individual scan lines, the means for calculating the boundary of the bone in the bone density image, and other details of the bone density calculation are well known and are not novel to the present invention. The means for intercepting the x-ray beam with a bone-like calibration material and calculating two baselines at portions of the body having only flesh, to calibrate the system, has many advantages.

Figure 7:
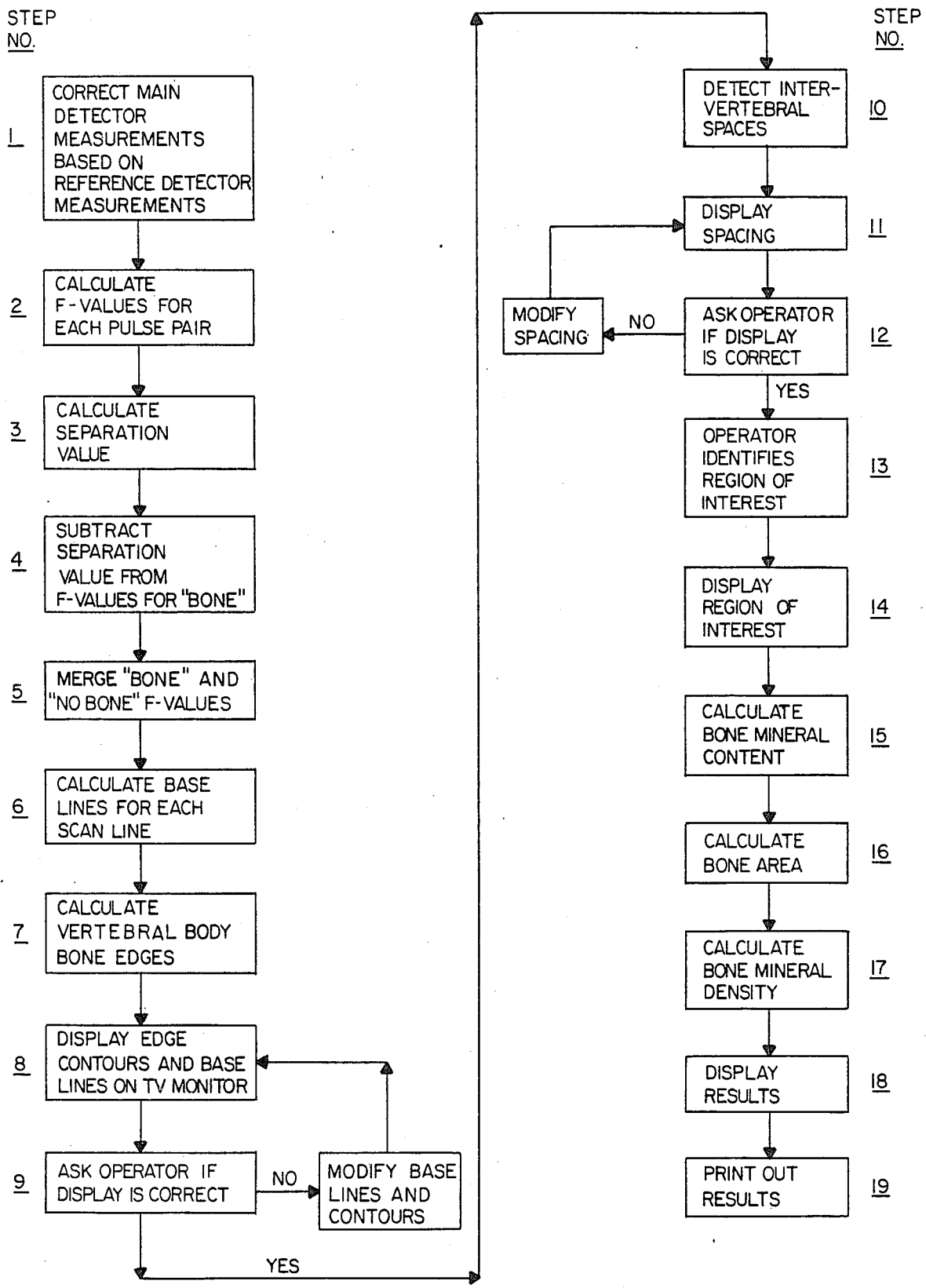
FIGS. 7, 7a and 7b represent a flow diagram of the calculations performed by the computer for examination of a spine.
Figure 7A:
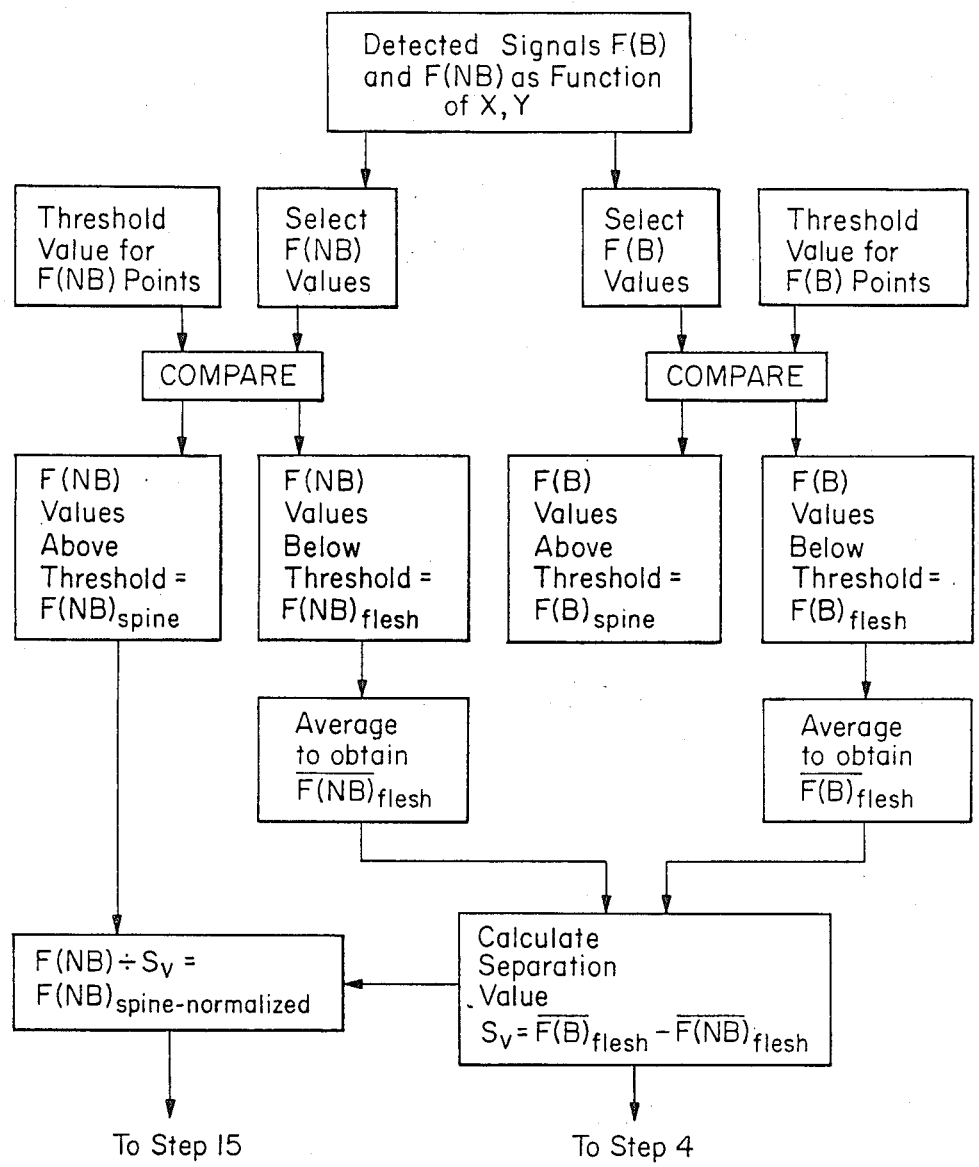
Figure 7B:
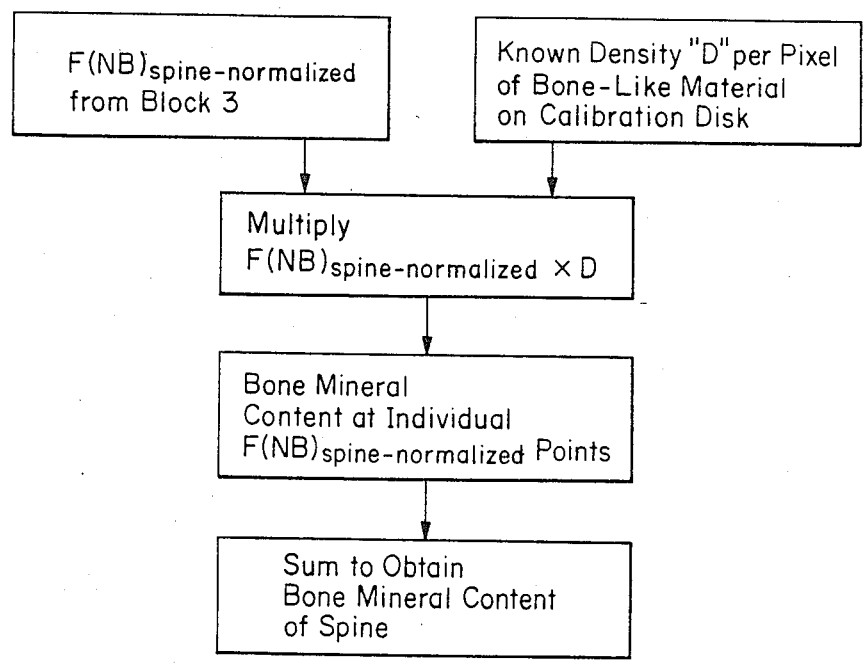

FIG. 7 is a flow diagram illustrating the steps performed by computer system 13 to calculate bone mineral content of the spine while FIG. 7a diagrams the steps of the calibration routine, block 3 of FIG. 7 and FIG. 7b diagrams the routine for calculation of bone mineral content.

For calibration, step 3, the program examines the data and decides which points in the scan form part of the spine and which do not. In other words, it distinguishes "spine" points from "flesh" points. It achieves this very simply by setting respective thresholds for F(N) and F(NB) values and defines all values above the threshold as "spine" points and all values below the threshold as "flesh" points.

The program then subtracts the F(NB) points that overlay flesh from the F(B) points that overlay flesh to calculate the separation value $S_L$ shown in FIG. 6 as distance 16. The average of the separation values averaged over all such subtracted pairs of points is then used as a calibration constant for Step 15 of FIG. 7 to calibrate the bone mineral content, see FIG. 7b. If the separation value changes by two percent, for example, from one day to another because of x-ray tube drift then the uncalibrated bone mineral content will change by two percent but the calibrated bone mineral content will remain constant.

Most of the steps shown in FIG. 7 are self-explanatory but some additional explanation is helpful. After the separation value, calculated in Step 3, is subtracted from the F values for "bone", there is no longer any distinction between the F values for "bone" and "no bone" and these two sets of F values may be merged into a single set in order to increase the spatial resolution achieved by doubling the number of points used to create the bone image (Steps 4 and 5).

In Step 7, the edges of the spinal vertebral bodies are found because FIG. 7 illustrates the flow sequence for measuring bone mineral density of the spine. For measurements of other bones, such as the hip, a different edge detection routine would be used. Between Steps 8 and 9 and between Steps 11 and 12, the operator is given an opportunity to modify the parameters calculated by the computer and to correct the parameters based on viewing the bone mineral image display. In Step 13 the operator decides which vertebral bodies will be included in the region of interest used to calculate bone mineral content and bone mineral density.

What is claimed is:

1. A bone densitometer for measuring bone content in a patient comprising an x-ray tube means and associated power supply which generates an x-ray beam, means to expose to the x-ray beam a part of a patient that includes regions having bone and adjacent regions having only flesh, means to insert into an remove from the x-ray beam a piece of bone-like calibration material of predetermined constant thickness such that said regions of the patient are exposed both to the x-ray beam and to the beam obstructed by said predetermined thickness of bone-like calibration material, detector means arranged on the opposite side of the patient to detect x-rays and produce signals corresponding to the amount of x-rays transmitted through the patient, and signal processing means responsive to signals from the detector means to produce a measurement of bone content based upon the signals produced by the exposure to the x-ray beam and corrected on the basis of signals produced by said exposure to the x-ray beam obstructed by said predetermined thickness of bone-like calibration material.

2. The bone densitometer of claim 1 wherein said signal processing means is responsive to distinguish, from the set of signals produced by the x-ray beam, a subset of signals which corresponds to regions of the patient having only flesh, and said signal processing means being responsive to signals from said subset as the basis for producing the correction.

3. The bone densitometer of claim 1 wherein the means to expose said regions to said x-ray beam is a scanning means constructed to scan said beam in a pattern over the patient and said means to insert said piece of bone-like calibration material is constructed and arranged to cause any point of the patient exposed to the unobstructed beam to lie substantially adjacent to a point exposed to the beam while obstructed by said bone-like calibration material.

4. The bone densitometer of claim 3 in which said means to insert and remove said predetermined thickness of bone-like calibration material is constructed to act on lines of scan distributed throughout the pattern of the scan.

5. The bone densitometer of claim 4 in which said x-ray tube means is constructed to produce a pencil beam and said beam pattern is a raster scan pattern.

6. The bone densitometer of claim 5 in which said means to insert and remove said piece of bone-like calibration material comprises a rotating carrier constructed to repeatedly carry said piece of material into and out of the beam during every line of scan of said pattern.

7. The bone densitometer of any of the claims 9, 10 or 1–6 wherein said power supply comprising means for applying alternate high and low voltage levels to said x-ray tube.

8. The bone densitometer of any of the claims 1–5, wherein the means to inset said piece of bone-like calibration material into the x-ray beam comprises a rotating carrier which carries said piece into and out of the x-ray beam.

9. The bone densitometer of claim 1 having a pencil beam collimator arranged to form and direct a pencil beam of x-rays through the patient, said detector means aligned with the collimator to detect x-rays attenuated by the patient, said x-ray tube, pencil beam collimator and detector means driven in unison in an X-Y raster scan pattern relative to the patient, scanning over portions of the patient having bone and adjacent portions having only flesh, and constantly rotating means for causing the beam to pass repeatedly through said bone-like calibration material in the course of the scan.

10. The bone densitometer of claim 9 where said signal processing means is responsive to data based upon x-rays passing through regions having only flesh to produce the correction.

11. The bone densitometer of claim 9, 10 or 3 wherein the scan pattern is limited to an area within the outer dimensions of the patient.

12. The bone densitometer of claim 9 wherein said power supply is constructed to apply alternate high and low voltage levels to said x-ray tube.

13. The bone densitometer of claim 12 wherein a control means for controlling the frequency of alternating said voltage is dependent upon the speed at which said x-ray tube, collimator and detector means are driven in scan motion and the beam width produced by said collimator such that said control means applies alternating high and low voltage levels to the x-ray tube at a frequency sufficiently high that at least one pair of high and low level exposures occurs during the short time period during which the pencil beam traverses a distance equal to about one beam width.

14. The bone densitometer of claim 13 constructed to produce pairs of high and low voltage pulses at a rate of the order of sixty per second, said x-ray tube, collimator and detector means being driven along said scan at a rate of the order of one inch per second and said collimator produces a pencil beam of between about one and three millimeters in diameter.

15. The bone densitometer of claim 14 constructed to cause said power supply to supply alternate high and low voltage to said x-ray tube and said x-ray beam passes through said bone-like calibration material for the duration of every other high and low voltage pulse pair.

16. The bone densitometer of claims 9, 10, 12, 13, 14 or 1 wherein said detector means comprises an integrating detector controlled to integrate the detected signal repeatedly over time periods that are short relative to the time required to advance the x-ray scan pattern by one pixel of resolution.

17. The bone densitometer of claim 16 including an analog to digital converter to converter each integrated value to a digital signal and a digital computer means for producing said measurement of bone content of the patient by processing a stream of said digital signals.

18. The bone densitometer of claim 9, 10, 13, or 14 including a reference system having at least two reference detectors, each provided with a different absorber, said reference system correcting for both x-ray tube current and voltage changes.

19. The bone densitometer of claim 18 constructed to correct said output of said detector means substantially on the basis of a function of the signals produced by said reference detectors.

20. The bone densitometer of claim 19 wherein there are two of said reference detectors and said function is substantially a straight line defined by the detected signals of said reference detectors.

21. The bone densitometer of claim 13 wherein said x-ray beam passes through said bone-like calibration material at least once per scan line for a period during which the pencil beam moves less than about one beam width and wherein said detector means comprises an integrating detector controlled to integrate the detected signal repeatedly over short time periods relative to the time required to advance said x-ray tube in its scan by one pixel of resolution.

22. The bone densitometer of claim 13 wherein said x-ray beam passes through said bone-like calibration material at least once per scan line for a period during which the pencil beam moves less than about one beam width and a reference system having at least two reference detectors each provided with a different absorber, said reference system correcting for both x-ray tube current and voltage changes.

23. The bone densitometer of claim 13 wherein said detector means comprises an integrating detector controlled to integrate the detected signal repeatedly over short time periods relative to the time required to advance said x-ray tube in its scan by one pixel of resolution and a reference system having at least two reference detectors each provided with a different absorber, said reference system constructed to correct for both x-ray tube current and voltage changes.

24. The bone densitometer of claim 13 wherein said x-ray beam passes through said bone-like calibration material at least once per scan line for a period during which the pencil beam moves less than about one beam width, said detector means comprises an integrating detector controlled to integrate the detected signal repeatedly over short time periods relative to the time required to advance said x-ray tube in its scan by one pixel of resolution, and a reference system having at least two reference detectors each provided with a different absorber, said reference system constructed to correct for both x-ray tube current and voltage changes.

25. The bone densitometer of claim 9, 10, 12, 13 or 14 in which the bone-like calibration material is rotated on a disc that causes a pencil beam to periodically pass through the calibration material for a period sufficiently small that the distance traversed by the pencil beam during the interruption is not more than about one beam width.

26. The bone densitometer of claim 25 wherein said detector means comprises an integrating detector controlled to integrate the detected signal repeatedly over short time periods relative to the time required to advance said x-ray tube in its scan by one pixel of resolution.

27. The bone densitometer of claim 25 including a reference system having at least two reference detectors each provided with a different absorber, said reference system constructed to correct for both x-ray tube current and voltage changes.

28. The bone densitometer of claim 25 wherein said detector means comprises an integrating detector controlled to integrate the detected signal repeatedly over short time periods relative to the time required to advance said x-ray tube in its scan by one pixel of resolution, a reference system having at least two reference detectors each provided with a different absorber, said reference system constructed to correct for both x-ray tube current and voltage changes.

29. A method of measuring bone content in a patient who is held in fixed position comprising:
   generating an x-ray beam,
   scanning the patient by passing the x-ray beam through portions of the patient having bone and adjacent portions having only flesh,
   passing the x-ray beam through a bone-like calibration material having a predetermined constant thickness in the course of scanning the patient such that portions of the patient are exposed both to an unobstructed x-ray beam and to a beam obstructed by said thickness of bone-like calibration material,
   detecting x-rays attenuated by the patient,
   calibrating signals from detected x-rays using data based upon x-rays attenuated by said calibration material in regions having only flesh, and
   processing signals from detected x-rays to provide a measurement of bone content in the patient.

30. The method of claim 29 comprising the further step of driving said x-ray beam in an X-Y raster scan pattern relative to the patient.

31. The method of claim 30 further comprising periodically passing said x-ray beam through said bone-like calibration material a multiple number of times per scan line.

32. The method of claim 29 or 30 further comprising passing said x-ray beam through said bone-like calibration material at least once per scan line.

33. The method of claim 29 or 30 wherein the signal calibrating comprises selecting data based upon x-rays attenuated by said calibration material in regions adjacent to bone.

34. The method of claim 29 or 30 further comprising restraining said x-ray tube from scanning beyond the outer dimensions of the patient.

35. The method of claim 29 or 30 further comprising applying alternating high and low voltage levels to an x-ray generation means to generate said x-ray beam.

36. The method of claim 29 or 30 further comprising:
   attenuating portions of said x-ray beam with at least two different reference absorbers,
   detecting x-rays attenuated by said reference absorbers, and
   correcting for variations in said x-ray beam using signals detected from x-rays attenutated by said reference absorbers.

* * * * *

UNITED STATES PATENT AND TRADEMARK OFFICE
CERTIFICATE OF CORRECTION

PATENT NO. : 4,811,373

DATED : March 7, 1989

INVENTOR(S) : Stein

It is certified that error appears in the above-identified patent and that said Letters Patent is hereby corrected as shown below:

Col. 1, line 2, "bone like" should be --bone-like--.
Col. 1, line 54, "non bone" should be --non-bone--.
Col. 1, line 68, "bone like" should be --bone-like--.
Col. 2, line 4, "film like" should be --film-like--.
Col. 2, line 20, "X Y" should be --X-Y--.
Col. 2, line 61, Delete "," after "value".
Col. 2, line 63, "cf" should be --of--.
Col. 4, line 7, "X ray" should be --X-ray--.
Col. 4, line 26, "X ray" should be --X-ray--.
Col. 4, line 32, "X Y" should be --X-Y--.
Col. 8, line 64, "no bone" should be --no-bone--.
Col. 10, line 6, "san" should be --scan--.
Col. 10, line 20, "pre determined" should be --pre-determined--.
Col. 11, lines 1-2, "no bone" should be --no-bone--.

Signed and Sealed this

Fourteenth Day of November, 1989

*Attest:*

JEFFREY M. SAMUELS

*Attesting Officer*    *Acting Commissioner of Patents and Trademarks*

UNITED STATES PATENT AND TRADEMARK OFFICE
CERTIFICATE OF CORRECTION

PATENT NO.   : 4,811,373
DATED        : March 7, 1989
INVENTOR(S)  : Jay A. Stein It is certified that error appears in the above-identified patent and that said Letters Patent is hereby corrected as shown below:

Col. 1, line 4, insert, --This application is a continuation-in-part of U.S. Serial No. 885,098, filed July 14, 1986.--

Signed and Sealed this

Sixteenth Day of January, 1990

Attest:

JEFFREY M. SAMUELS

*Attesting Officer*   *Acting Commissioner of Patents and Trademarks*